United States Patent
Subrebost et al.

(10) Patent No.: US 8,246,541 B2
(45) Date of Patent: Aug. 21, 2012

(54) REAL-TIME MICRODIALYSIS SYSTEM

(75) Inventors: George Lopez Subrebost, Swissvale, PA (US); Alan J. Rosenbloom, Pittsburgh, PA (US); Heer Gandhi, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/256,084

(22) PCT Filed: Apr. 7, 2010

(86) PCT No.: PCT/US2010/030263
§ 371 (c)(1),
(2), (4) Date: Sep. 12, 2011

(87) PCT Pub. No.: WO2010/118150
PCT Pub. Date: Oct. 14, 2010

(65) Prior Publication Data
US 2012/0016216 A1 Jan. 19, 2012

Related U.S. Application Data

(60) Provisional application No. 61/212,074, filed on Apr. 7, 2009.

(51) Int. Cl.
*A61B 5/00* (2006.01)
*A61B 5/05* (2006.01)
(52) U.S. Cl. ......................... 600/365; 600/407
(58) Field of Classification Search .................. 600/316, 600/345, 347, 365, 366, 407
See application file for complete search history.

(56) References Cited

U.S. PATENT DOCUMENTS

| | | | |
|---|---|---|---|
| 5,640,954 | A | 6/1997 | Pfeiffer et al. |
| 2002/0082490 | A1* | 6/2002 | Roeper et al. .................. 600/347 |
| 2004/0168934 | A1 | 9/2004 | Schaupp et al. |
| 2005/0209518 | A1 | 9/2005 | Sage, Jr. et al. |

(Continued)

FOREIGN PATENT DOCUMENTS

WO WO 2004/111209 A1 12/2004

OTHER PUBLICATIONS

Stenken, J. A. 2006. Microdialysis Sampling. Encyclopedia of Medical Devices and Instrumentation.*

(Continued)

*Primary Examiner* — Charles Marmor
*Assistant Examiner* — Christian Jang
(74) *Attorney, Agent, or Firm* — K&L Gates LLP (57) ABSTRACT

Microdialysis systems and methods that enable self-diagnostic functions for microdialysis, including continuous monitoring of diffusion, convection, and osmosis, as well as providing intelligent flow rate control, to mitigate variability in analyte recovery. The microdialysis system measures real-time tracer concentration levels in the dialysate and/or real¬time flow rates of the dialysate. A control circuit may compute the real-time tracer concentration levels in the dialysate and/or real-time flow rates of the dialysate based on real¬time tracer concentration data from an in-line tracer concentration meter and real-time flow rate data from an in-line flow rate meter. Analyte concentration data for the dialysate may also be measured using an analyte concentration meter. The control circuit may compute a corrected analyte concentration for the dialysate based on the analyte concentration data, the tracer concentration data, and the flow rate data in various embodiments.

40 Claims, 5 Drawing Sheets

U.S. PATENT DOCUMENTS

| | | | |
|---|---|---|---|
| 2007/0106140 A1* | 5/2007 | Bellantone | 600/366 |
| 2007/0110625 A1 | 5/2007 | Krishnamoorthy et al. | |
| 2007/0292958 A1 | 12/2007 | Lacourse et al. | |
| 2008/0146896 A1 | 6/2008 | Rabinowitz et al. | |
| 2008/0153118 A1 | 6/2008 | Quarder et al. | |
| 2008/0176271 A1 | 7/2008 | Silver et al. | |
| 2009/0054908 A1 | 2/2009 | Zand et al. | |
| 2009/0082566 A1* | 3/2009 | Mitra | 544/276 |

OTHER PUBLICATIONS

Li, Z.; Boubriak, O. A.; Urban, J. P.; Cui, Z. F. "Microdialysis for monitoring the process of functional tissue culture," International Journal of Artificial Organs (2006), 29(9), 858-865.

Boubriak, O. A.; Urban, J. P. G.; Cui, Z. F., "Monitoring of lactate and glucose levels in engineered cartilage construct by microdialysis," Journal of Membrane Science (2006), 273(1-2), 77-83.

Wisniewski, Natalie; Klitzman, Bruce; Reichert, William M; "Membrane biofouling measured by microdialysis," Proceedings of the International Symposium on Controlled Release of Bioactive Materials (1998), 25th 73-74.

Wisniewski N, Klitzman B, Miller B, Reichert WM., "Decreased analyte transport through implanted membranes: differentiation of biofouling from tissue effects," Journal of Biomedical Materials Research, Dec. 15, 2001;57(4):513-21.

Damm, Uwe; Kondepati, Venkata Radhakrishna; Heise, H. Michael, "Continuous reagent-free bed-side monitoring of glucose in biofluids using infrared spectrometry and micro-dialysis," Vibrational Spectroscopy (2007), 43(1), 184-192.

Ricci, Francesco; Moscone, Danila; Palleschi, Giuseppe, "Ex vivo continuous glucose monitoring with microdialysis technique: the example of GlucoDay," IEEE Sensors Journal (2008), 8(1), 63-70.

Subrebost,G., "Silicon-based microdialysis chip with integrated fraction collection and biofouling control," Subrebost Ph.D. Thesis, The Robotics Institute, Carnegie Mellon University 2005.

Bungay, P., "Utilizing transmembrane convection to enhance solute sampling and delivery by microdialysis: Theory and in vitro validation," Journal of Membrane Science (2010), 348, 131-149.

Hsieh, Y., Ph.D., "On-chip Microdialysis System with Flow-Through Glucose Sensing Capabilities," Journal of Diabetes Science and Technology, vol. 1, Issue 3, May 2007.

International Search Report and Written Opinion for PCT/US2010/030263, Jun. 17, 2010 (13 pages).

* cited by examiner

REAL-TIME MICRODIALYSIS SYSTEM

PRIORITY CLAIM

This application claims priority to U.S. provisional patent application Ser. No. 61/212,074, filed Apr. 7, 2009, titled "Microdialysis system and device," which is incorporated herein by reference.

BACKGROUND

Microdialysis is an extremely versatile technique for sampling from blood and tissues in living animals and humans. A small probe, similar to a very thin intravenous needle (approximately one-half millimeter diameter) is inserted via needle stick. The probe has porous walls and an internal buffer flowing through it. Molecules enter the probe by diffusion and then are carried out to be measured.

Microdialysis has many appealing features, including that it is minimally invasive and remarkably versatile. It has been a valuable research tool in studying neurotransmitters in the brain, performing studies of drug distribution in tissues and blood, and many other purposes. Nevertheless, microdialysis has remained predominantly a research tool for over two decades because there are several problematic issues intrinsic to microdialysis systems that prevent it from becoming a robust clinical tool. One issue is that microdialysis probes are prone to fouling (or biofouling), which is a process that starts immediately upon contact of a synthetic material with the body, when cells, proteins, blood clots and other biological components adhere to the surface of the foreign material. Fouling remains a problem for any separation medium since it can significantly reduce acquisition of biomolecules, such as glucose. Within tissue other processes such as scar formation and cellular attack also slowly degrade the access of sensors to the surrounding interstitial fluid.

Another issue with microdialysis involves the undesirable phenomenon of water transport across the membrane by ultrafiltration (differential hydrostatic pressure) and osmosis (which is diffusion-based movement of water molecules). Ultrafiltration into the probe will augment analyte recovery while ultrafiltration out of the probe will reduce recovery. Both increase variability. The larger pore membranes used to capture macromolecules, such as proteins and nucleic acids, are particularly prone to ultrafiltration/osmosis. Ultrafiltration/osmosis during microdialysis is currently not measured in a real-time fashion.

Another issue is that the recovery of molecules via microdialysis, their transport through the system and their analysis by on-board detectors, is affected by flow rate. The slower the flow rate, the higher the recovery of analyte molecules from the surrounding medium since more time is allowed for transport across the membrane. Although many have experimented with different flow rates, there is no "intelligent" control circuit to optimize flow rates in microdialysis systems.

Because of these complications, microdialysis systems can fail or give unreliable data. Consequently, although some have used microdialysis for studies in the injured human brain, and for continuously monitoring glucose in the blood, clinical devices that take advantage of microdialysis have not evolved.

SUMMARY

In one general aspect, embodiments of the present invention are directed to microdialysis systems and methods that enable self-diagnostic functions for microdialysis, including continuous monitoring of diffusion, convection, and osmosis, as well as providing intelligent flow rate control, to mitigate variability in analyte recovery. This permits microdialysis to move from a research tool to a robust, clinically-useful modality. The microdialysis system measures real-time tracer concentration levels in the dialysate and/or real-time flow rates of the dialysate. A control circuit, that may comprise a processor-based microcontroller, may compute the real-time tracer concentration levels in the dialysate and/or real-time flow rates of the dialysate based on real-time tracer concentration data from an in-line tracer concentration meter and real-time flow rate data from an in-line flow rate meter. In various embodiments, analyte concentration data for the dialysate may also be measured using an analyte concentration meter. The control circuit may compute a corrected analyte concentration for the dialysate based on the analyte concentration data, the tracer concentration data, and the flow rate data in various embodiments.

The microdialysis system may continuously monitor fouling of the membrane pores of the microdialysis probe by using real-time detectable tracer molecules in the perfusate. The real-time detectable tracer molecules are preferably fluorescent, although tracer molecules with other real-time detectable characteristics may be used as well, as explained below. A decrease in tracer diffusion rate quantitates loss of diffusion capacity. If the inlet tracer level (from the supply pump before the microdialysis probe) approaches the outlet tracer level in the dialysate, then fouling is obstructing the pores. In addition, excess fluid being added to or removed from the microdialysis probe, caused by ultrafiltration or osmosis, can be detected by measuring dialysate flow rate and comparing it to the supply pump flow rate.

These and other benefits of the present invention will be apparent from the description below.

DESCRIPTION OF THE FIGURES

Various embodiments of the present invention are described herein in conjunction with the following figures, wherein.

DESCRIPTION

Figure 1:
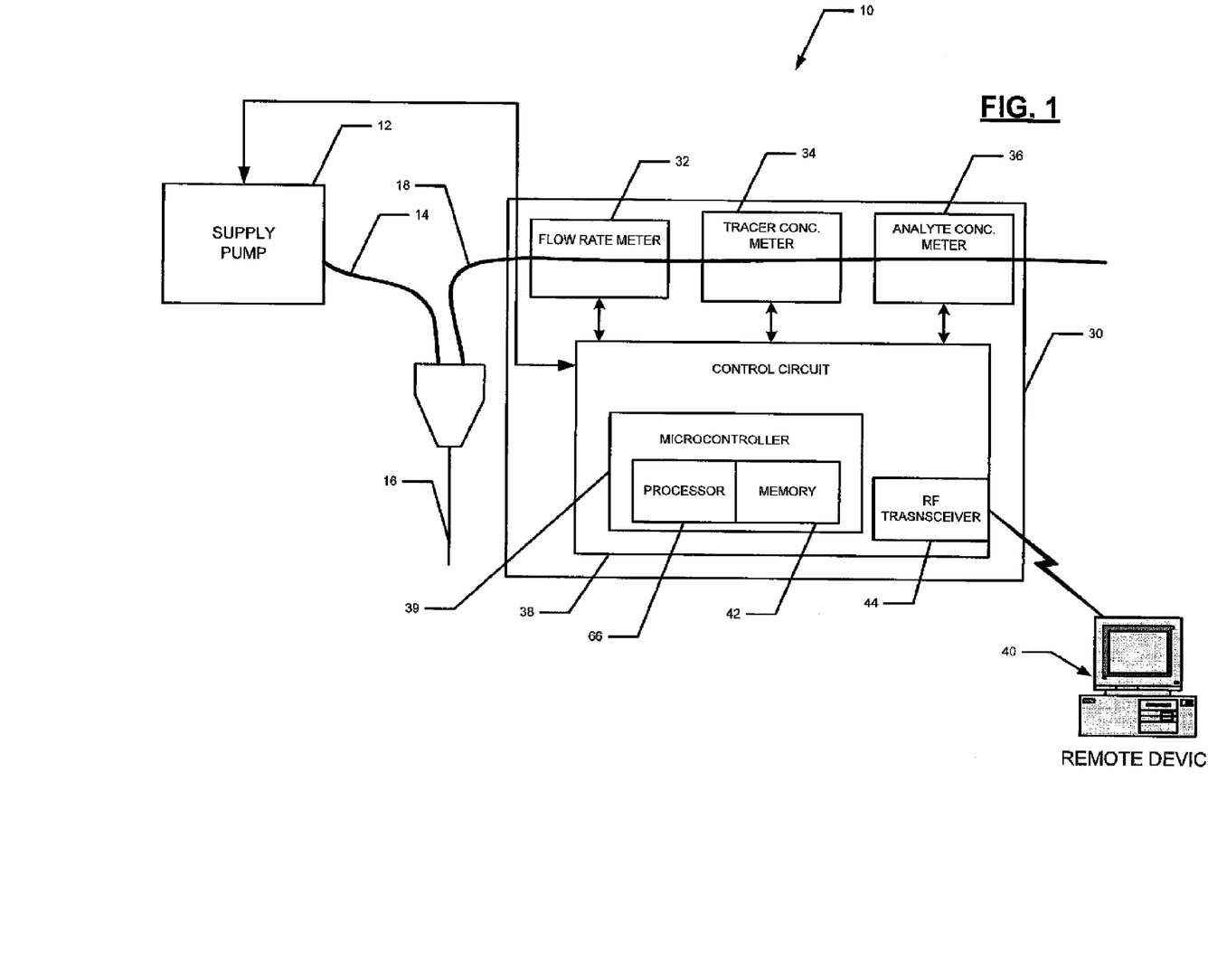
FIG. 1 is a diagram of a microdialysis system according to various embodiments of the present invention.
Figure 2:
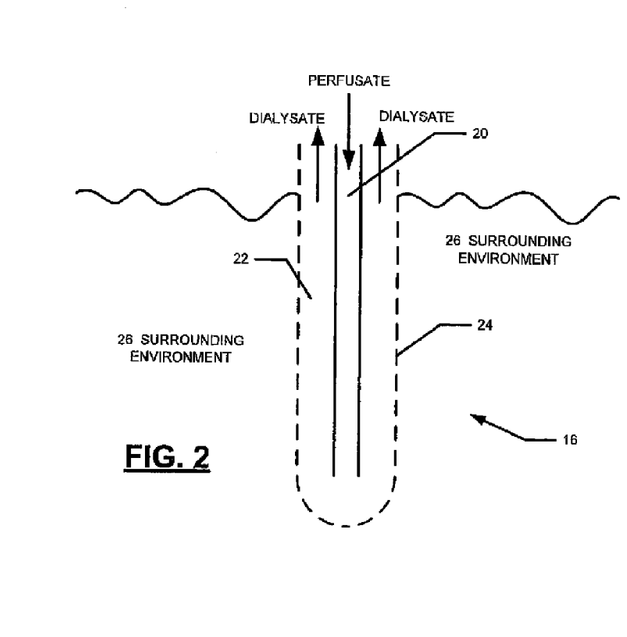
FIG. 2 is a diagram of a microdialysis probe of the microdialysis system according to various embodiments of the present invention.
Figure 5:
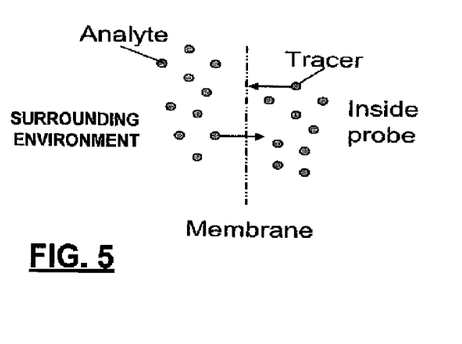
FIG. 5 is a diagram of analyte molecules and tracer molecules diffusing across the membrane of the microdialysis probe of the microdialysis system.

FIG. 1 is a diagram of a microdialysis system 10 according to various embodiments of the present invention. A supply pump 12 pumps a microdialysis perfusate (also sometimes referred to as a buffer solution) via an inlet 14 to a microdialysis probe (or catheter) 16. The perfusate may comprise real-time detectable tracer molecules, examples of which are described below. The microdialysis probe 16, as shown in FIG. 2, may comprise a central passageway 20 and a peripheral passageway 22 that circumferentially surrounds the central passageway 20. The microdialysis probe 16 also comprises a semi-permeable outer membrane 24. The perfusate (or buffer solution) from the supply pump 12 may flow down through the central passageway 20 and then up through the peripheral passageway 22. As the perfusate flows through the peripheral passageway 22, tracer molecules in the perfusate may diffuse across the membrane 24 into the surrounding environment 26 as the perfusate is pumped through the microdialysis probe 16. Similarly, analyte molecules in the surrounding environment 26 may diffuse across the membrane 24 into the microdialysis probe 16. This is also shown in FIG. 5, which diagrammatically shows diffusion of analyte molecules into the probe 16 and diffusion of tracer molecules out of the probe 16. The surrounding environment 26 may be tissue or vein of a mammal, into which the probe 16 is inserted or implanted. The dialysate in the peripheral passageway 22, comprising the perfusate with the analyte molecules from surrounding environment 26 and less the portion of the tracer molecules that diffused through the membrane 24 to the surrounding environment 26, is collected and pumped via an outlet (also sometimes referred to herein as "dialysate tubing") 18 to a measuring device 30 (see FIG. 1). The measuring device 30 may measure the real-time (or continuous) flow rate and/or the real-time tracer concentration of the dialysate. The measuring device 30 may also measure the concentration of the analyte in the dialysate. In addition, in various embodiments, the measuring device 30 may compute a corrected real-time concentration of the analyte in the dialysate, considering, for example, the flow rate of the dialysate and the tracer concentration of the dialysate.

The supply pump 12 may comprise any suitable pump for supplying the perfusate to the microdialysis probe 16, such as a syringe pump, an intravenous pump, or an implantable infusion pump, for example. The supply pump 12 may pump the perfusate at settable volume flow rates ranging from 0.1 to 10 µL/min, for example. In various embodiments, the supply pump 12 may comprise or be similar to a CMA 107 microdialysis pump available from CMA Microdialysis AB, Solna, Sweden. The microdialysis probe 16 may comprise or be similar to, for example, a CMA 64 iView microdialysis catheter available from CMA Microdialysis AB. The microdialysis probe 16 may have a diameter of 0.5 mm, for example.

As shown in FIG. 1, the measuring device 30 may comprise a flow rate meter 32, a tracer concentration meter 34, an analyte concentration meter 36, and a processor-based electronic control circuit 38. The flow rate meter 32 measures the real-time flow rate of the dialysate in the dialysate tubing 18. The tracer concentration meter 34 measures the real-time concentration of the tracer in the dialysate tubing 18. The concentration of the tracer in the dialysate may be indicative of the diffusion rate of the membrane 24 of the microdialysis probe 16. If the diffusion rate of the tracer out of the microdialysis probe 16 is related to the diffusion rate of the analyte from the surrounding environment 26 in the microdialysis probe 16, the tracer concentration can be indicative of the diffusion rate of the analyte. The diffusion rate can change over time, such as because of fouling of the pores of the membrane 24. Thus, the tracer concentration can be indicative of the amount of probe membrane fouling. The analyte concentration meter 36 measures the real-time concentration of an analyte in the dialysate tubing 18. The control circuit 38 may control functions and operations of the flow rate meter 32, the tracer concentration meter 34, and/or the analyte concentration meter 36. In addition, the control circuit 38 may receive flow rate data from the flow rate meter 32, tracer concentration data from the tracer concentration meter 34, and analyte concentration data from the analyte concentration meter 36. Based on the received data, the control circuit 38 may calculate, for example, the real-time flow rate of the dialysate, the real-time tracer concentration of the dialysate, and/or a corrected real-time analyte concentration, considering the tracer concentration and the flow rate of the dialysate in addition to the analyte concentration data from the analyte concentration meter 36. The control circuit 38 may comprise, for example, a microcontroller 39 as well as other circuit components mounted to a printed circuit board.

In various embodiments, the analyte may be glucose, in which case glucose molecules in the surrounding environment 26 (e.g., blood) of the microdialysis probe 16 may diffuse through the probe membrane 24, and the measuring device 30 may measure in real-time the concentration of the analyte in the dialysate. In such a manner, the microdialysis system 10 could be used for tight blood glucose control (TGC). TGC requires frequent determination of blood glucose that is accurate and rapidly available. Present technology for obtaining these readings is by the use of point-of-care glucose meters and fingerstick blood sampling. This method has been shown to be unreliable in critically ill patients and has been suspected of causing inaccurate insulin doses that lead to harmful glucose levels for patients. Present techniques for acquiring the readings are also expensive and time consuming for the nursing staff and uncomfortable for the patient. On the other hand, continuous blood glucose monitoring with the microdialysis system 10 can eliminate repeated testing and allow adjustment of glucose levels more smoothly, quickly, and with increased safety.

In an embodiment where the measuring device 30 is used to determine the analyte glucose concentration in the dialysate, the analyte concentration meter 36 may comprise a glucose monitor. In various embodiments, the glucose monitor may comprise or be similar to, for example, a CGMS iPro glucose monitor available from Medtronic, Inc., Minneapolis, Minn.

To account for probe membrane fouling, a real-time detectable tracer in the perfusate may be used. According to various embodiments, the tracer may be fluorescent, electrochemical, radioactive, or have some other characteristic that is detectable by the tracer concentration meter 34 in real time. For example, if a fluorescent tracer is used, the tracer concentration meter 34 may have a fluorescence detection system (e.g., a fluorometer); if an electrochemical tracer is used, the tracer concentration meter 34 may have an electrical conductivity or amperometric detection system; and if a radioactive tracer is used, the tracer concentration meter 34 may have a radiation detection system.

Figure 3A:
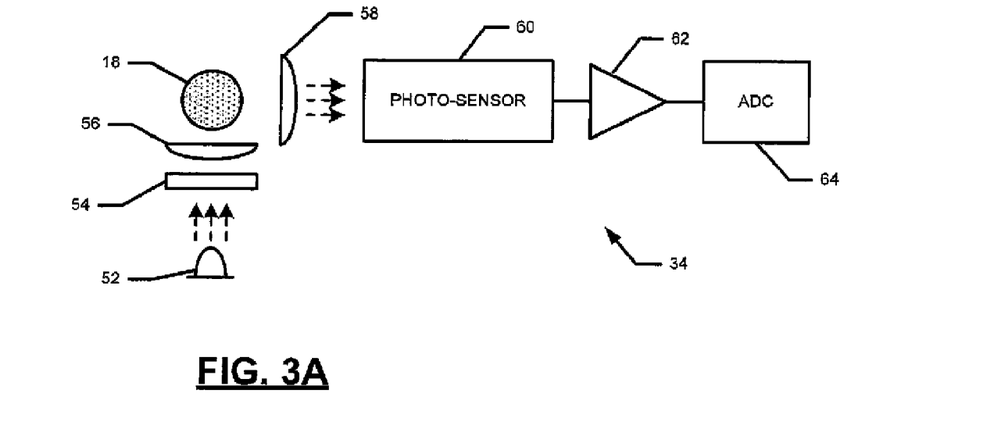
FIGS. 3A-3C are diagrams of tracer concentration meters of the microdialysis system according to various embodiments of the present invention.

In embodiments where the detectable tracer is fluorescent, the tracer concentration meter 34 may comprise, as shown in FIG. 3A, a light source 52, such as one or more light emitting diodes (LEDs), a filter 54 for filtering light energy emitted by the light source 52, and a lens 56, such as an aspheric lens, for focusing the filtered light energy from the light source 52 on the dialysate tubing 18. In various embodiments, the real-time detectable tracer of the perfusate may comprise fluorescein, although other suitable and approved fluorescent tracers may be used, such as riboflavin or indocyanine green (ICG), for example. The perfusate in such an embodiment may comprise calcium magnesium free-phosphate buffered saline (CMF-PBS) or Lactated Ringer's solution, for example. Fluorescein emits green light at a 521 nm wavelength when blue light (488 nm wavelength) is projected onto the fluorescein. Thus, the filtered light energy from the light source 52 may comprise light energy with wavelengths centered around or near 488 nm wavelength to excite the fluorescein tracer molecules in the dialysate. The light source 52 may be a broadband light source, and the filter 54 may filter out undesired wavelength bands. In other embodiments, a narrow-band light source 52 could be used (with the filter 54 possibly omitted). For example, the light source 52 may be a narrow-band light source emitting light energy in a narrow range of wavelengths, such as a laser, centered around or near 488 nm.

The tracer concentration meter 34 may also comprise a lens 58 and a photo-sensor 60. As shown in FIG. 3A, the lens 58 and photo-sensor 60 may be oriented ninety (90) degrees relative to the light source 52. Light emitted by the fluorescent tracer molecules in the dialysate may be focused by the lens 58 onto the photo-sensor 60. The lens 58 may be an aspheric lens. The photo-sensor 60 preferably comprises a CMOS imager, although other photo-sensors could also be used, such as a photodiode, a photomultiplier tube, and an avalanche photodiode, for example. For faster throughput and lower dead volumes, small diameter dialysate tubing 18 is preferred. For example, dialysate tubing 18 with a diameter of 150 microns may be used. Using such small diameter dialysate tubing, however, reduces the signal-to-noise ratio of the signal. For this reason, a CMOS imager for the photo-sensor 60 is preferred when small diameter dialysate tubing is used because a CMOS imager provides greater sensitivity than conventional photodiodes. Experimental testing has shown that with a CMOS imager, the signal-to-noise ratio can be improved to 4b dB using windowing, compared to 24 dB with a photodiode.

Figure 6:
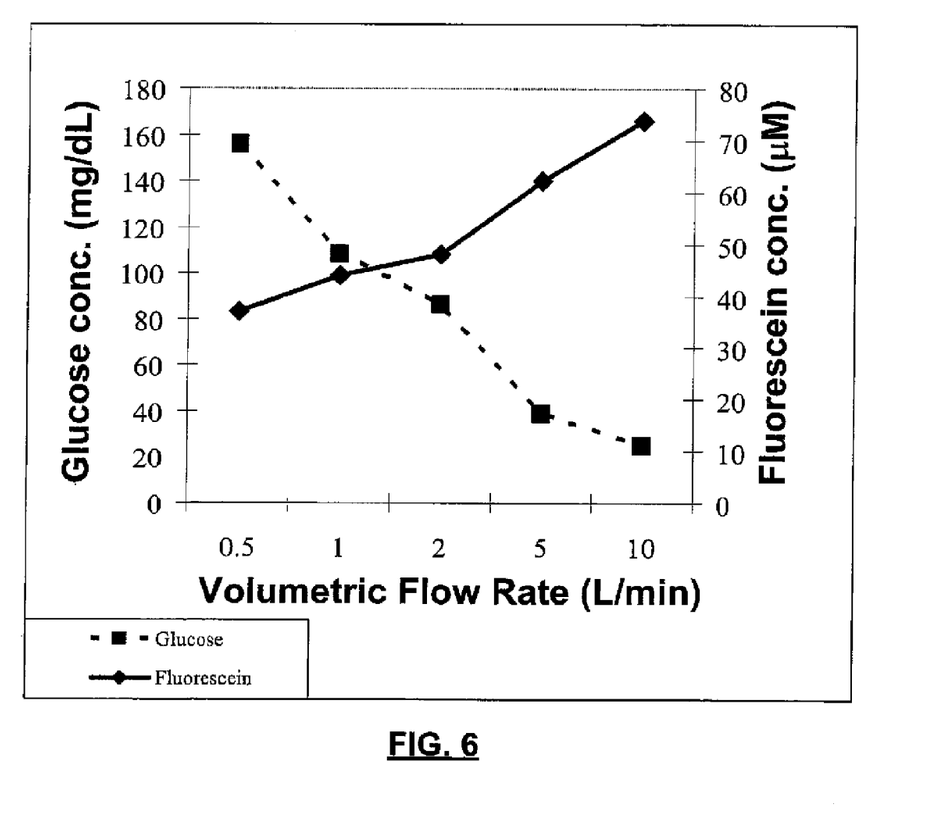
FIG. 6 shows experimental test results for in vitro glucose absolute recovery and fluorescein absolute loss by a microdialysis probe at varying volumetric flow rates.

The output of the photo-sensor 60 may be amplified by an amplifier 62 and sampled by an analog-to-digital converter (ADC) 64. The amplifiers 62 and the ADC 64 may be part of the control circuit 38, or they could be part of the tracer concentration meter 34. In various embodiments, the light source 62 is modulated and focused on the dialysate tubing 18 for a period of time, such as 500 ms. Within this time frame, the ADC 64 may be programmed to sample the amplified signal from the photo-sensor 60 for 2,560 samples. The sample outputs from the ADC may be input to a processor 66 (which may comprise a digital signal processor (DSP)) of the microcontroller 39 of the control circuit 38. The processor 66 may be programmed, with executable instructions in memory 42 of the microcontroller 39, to measure the average DC level and the AC RMS level of the samples. The analog gain of the amplifier 62 can be calibrated using this information and all the data henceforth may be measured relative to the calibrated signal. The AC RMS signal levels may denote the real-time fluorescence level, and hence the real-time tracer concentration, of the dialysate. The tracer concentration in turn may be related to the fouling of the probe membrane 24, which is related to the diffusion rate of the analyte, depending on the tracer and analyte employed. For example, FIG. 6 shows experimental test results for in vitro glucose absolute recovery and fluorescein absolute retention by a microdialysis probe at varying volumetric flow rates. For this experiment, the microdialysis probe was placed in a well of 180 mg/dL glucose while the perfusate contained 100 μM fluorescein. As FIG. 6 shows, the glucose absolute recovery decreased with increasing flow rate at approximately the same rate that the fluorescein absolute retention increased. Thus, the fluorescein concentration in the dialysate detected by the tracer concentration module 34 can be indicative of the diffusion capacity of probe membrane 24 and analyte concentration in the dialysate.

Figure 3B:
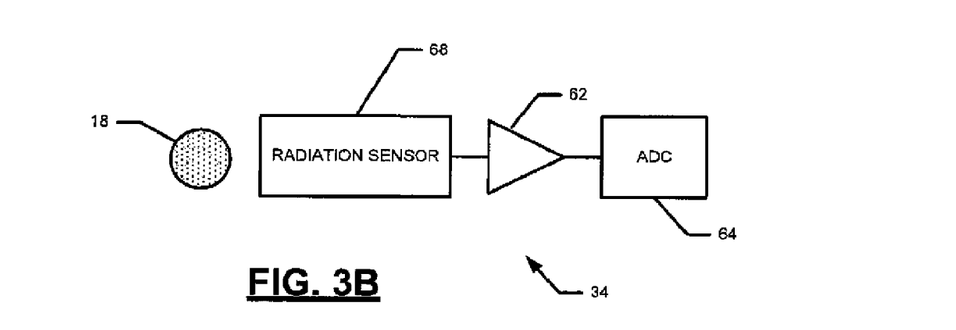
Figure 3C:
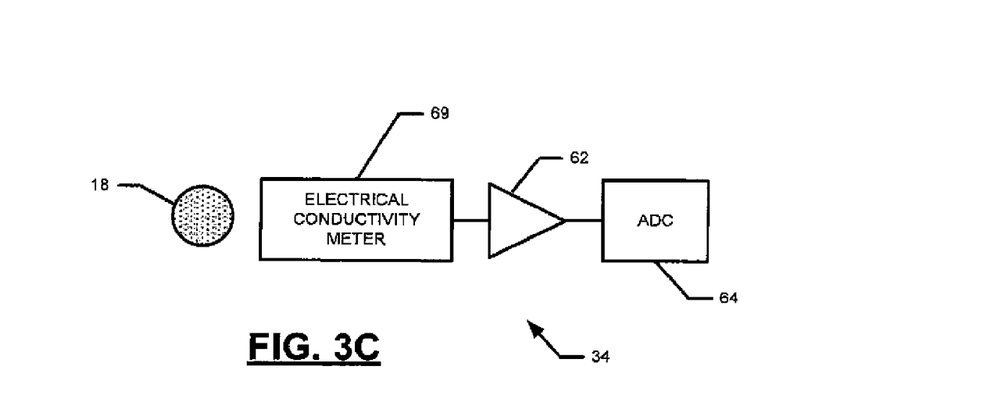

FIGS. 3B-3C diagrammatically show embodiments of the tracer concentration module 34 according to various other embodiments of the present invention. The embodiment of FIG. 3B may be used where radioactive tracer molecules are used. Such an embodiment may employ a radiation sensor 68 to detect the real-time radiation level of the dialysate to thereby determine the real-time tracer concentration of the dialysate. The embodiment of FIG. 3C may be used where electrochemical tracer molecules are used, such as electrolytes. Such an embodiment may employ an electrical conductivity sensor 69 to detect the real-time electrical conductivity level of the dialysate to thereby determine the real-time tracer concentration of the dialysate.

Figure 4A:
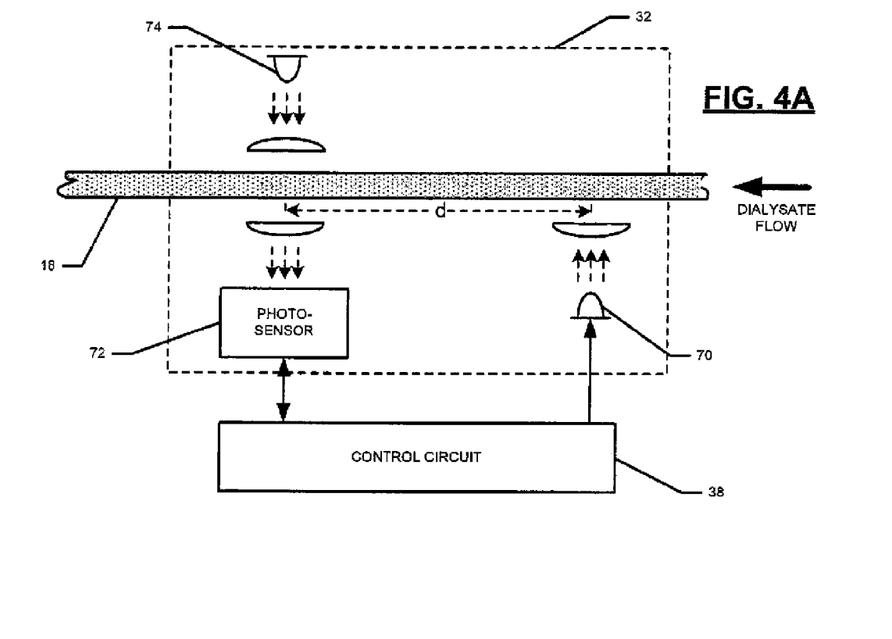
FIGS. 4A-4B are diagrams of flow rate meters of the microdialysis system according to various embodiments of the present invention.

FIG. 4A shows an embodiment of the flow rate meter 32 according to various embodiments. In the illustrated embodiment, the flow rate meter 32 periodically photobleaches the fluorescent in the dialysate tubing 18 to create a photobleached plug and measures how long time wise it takes for the photobleached plug to travel a known, fixed distance "d." In such an embodiment, the flow rate meter 32 may comprise a light source 70 that emits light energy on the dialysate tubing 18. The light source 70 may comprise, for example, a LED, such as a blue light LED (anywhere between 460 to 490 nm wavelength), particularly when the fluorescent is fluorescein. The light source 70 may be a known, fixed distance d upstream the dialysate tubing 18 from a photo-sensor 72. The light source 70 may have a higher intensity than the light source 52 of the tracer concentration meter 34.

The photo-sensor 72 preferably comprises a CMOS imager, although other photo-sensors could also be used, such as a photodiode, a photomultiplier tube, and an avalanche photodiode, for example for example, a CMOS imager or a photodiode. A second light source 74 may be aligned with the sensor 72, and opposite the dialysate tubing 18 from the sensor 72 to illuminate or excite the fluorescent tracer molecules in the dialysate. For example, the second light source 74 may emit light energy at about 488 nm wavelength when flourescein is used as the tracer. In one embodiment, the light source 52 of the tracer concentration meter 34 may be the same light source as light source 74 of the flow rate meter 32, such that one common light source is used for both the tracer concentration meter 34 and the flow rate meter 32. In other embodiments, separate light sources may be used for the tracer concentration meter 34 and the flow rate meter 32. In addition or alternatively, the photo-sensor 60 of the tracer concentration meter 34 may be the same photo-sensor as photo-sensor 72 of the flow rate meter 32, such that one common photo-sensor is used for both the tracer concentration meter 34 and the flow rate meter 32.

The light source 70, under control of the control circuit 38, may be pulsed periodically. The photo-sensor 72 may detect the fluorescence of the dialysate in the dialysate tubing 18 as it flows past the photo-sensor 72, the dialysate in the dialysate tubing 18 being simultaneously illuminated by the light source 74 for sensing by the photo-sensor 72. When the photobleached plug flows past the photo-sensor 72, the detected fluorescence in the dialysate decreases. The time period for the photobleached plug to flow from the distance d from the light source 70 (where the photobleached plug was created) to the photo-sensor 72, where it is detected, can be used by the control circuit 38 to determine the flow rate because of the known, fixed distance d between the light source 70 and the photo-sensor 72.

Output signals from the photo-sensor 72, indicative of the fluorescence of the dialysate, may be amplified (by an amplifier, not shown) and a sampled (by an ADC, not shown). The amplifier and/or ADC may be part of the control circuit 38, for example. The sampled output from the photo-sensor 72 may be input to the processor 66 of the microcontroller 39 of the control circuit 38, which, based on the digital samples and the known, fixed distance d between the source 70 and the sensor 72, may calculate the real-time volumetric flow rate of the dialysate based on the "time of flight" for the photobleached plug to travel the distance d between the source 70 and the sensor 72.

Changes in the flow rate may be caused by osmosis or convection at the microdialysis probe 16. The control circuit 38 may detect changes in the dialysate flow rate over time, and may also compare the current, real-time dialysate flow rate to the supply pump 12 pump rate for the perfusate. Differences between the flow rates indicate excess fluid being added to (if the dialysate flow rate is greater than the perfusate flow rate) or removed from (if the perfusate flow rate is greater than the dialysate flow rate) the probe 16.

Figure 4B:
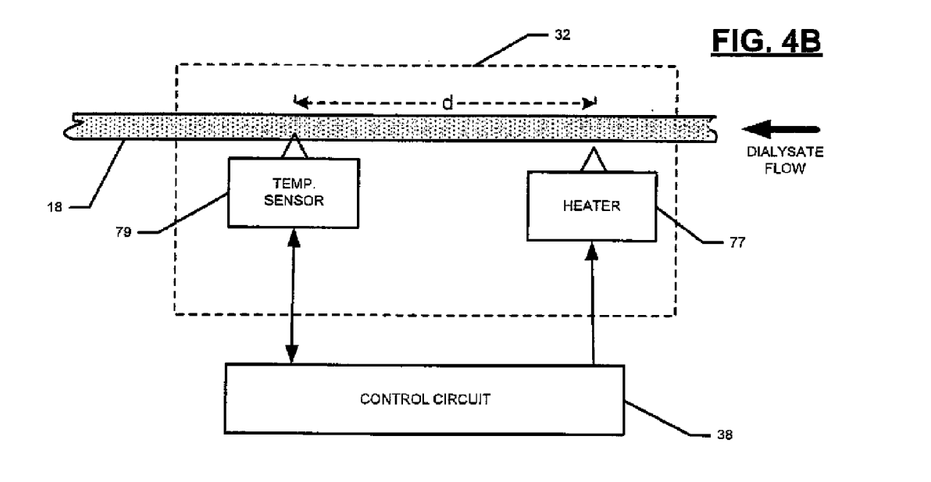

In other embodiments, different types of flow rate meters may be used. For example, in some embodiments, thermal flow rate meters may be used. In such an embodiment, as shown in FIG. 4B a heat source 77, such as an infrared photodiode, a laser, or some other suitable type of heater, may periodically heat dialysate in the dialysate tubing 18 to create a thermal plug. A temperature sensor 79 that is the fixed, known distance d downstream from the heat source 77 may detect the thermal plug in the dialysate tubing 18 as it flows past the temperature sensor 79. The control circuit 38 may determine the real-time volumetric flow rate of the dialysate based on the time period that it takes the thermal plug to travel the known distance d between the heat source 77 and the temperature sensor 79. For example, the temperature sensor 79 may be a CMOS infrared (IR) camera.

The control circuit 38 may control the sequence and operation of the flow rate and/or tracer concentration meters 32, 34. For example, the control circuit 38 may control the pulsing of the light sources 52, 70. In addition, the AC RMS values from the tracer concentration meter 34 may be stored in the memory 42 of the microcontroller 39 (see FIG. 1). Similarly, the calculated flow rate may be stored in the memory 42. The memory 42 may be any suitable data memory storage device, including, for example, random access memory (RAM), read only memory (ROM), programmable read only memory (PROM), electronically erasable PROM (EEPROM), flash memory, etc.

The control circuit may also receive analyte concentration data from the analyte concentration meter 36. The analyte concentration data may be stored in the memory 42. The processor 66 may utilize the analyte concentration data from the analyte concentration meter 36 to compute a corrected real-time analyte concentration of the dialysate, as explained below.

In various embodiments, the control circuit 38 may be in wireless communication with the flow rate meter 32, the tracer concentration meter 34, and/or the analyte concentration meter 36. In such embodiments, the control circuit 38 may communicate wirelessly with the flow rate meter 32, the tracer concentration meter 34, and/or the analyte concentration meter 36 using any suitable wireless communication protocol, such as ZigBee, Bluetooth, Wireless USB, etc. In addition, the control circuit 38 may be in (wired or wireless) communication with one or more remote computer devices 40 (see FIG. 1). Data from the control circuit 38, such as the AC RMS values from the tracer concentration meter 34, the flow rate data from the flow rate meter 32, the analyte concentration from the analyte concentration meter 36, and/or corrected analyte concentration values that are computed by the control circuit 38, may be uploaded to the remote device 40 from the control circuit 38. In various embodiments, the control circuit 38 may be powered by one or more battery cells, such as lithium ion battery cells, and/or by an external power source.

In various embodiments, the control circuit 38 may calibrate the analyte concentration meter 36 based on the tracer concentration data and/or the flow rate data. For example, the processor 66 of the microcontroller 39 of the control circuit 38 may compute calibrations for the analyte concentration meter 36 based on the tracer concentration data and/or the flow rate data, and the control circuit 38 may communicate the calibrations to the analyte concentration meter 36 in order to calibrate the analyte concentration meter 36. In addition, in various embodiments, the control circuit 38 (e.g., the processor 66) may compute a corrected analyte concentration level based on the analyte concentration data from the analyte concentration meter 36, considering the tracer concentration data from the tracer concentration meter 34 and the flow rate data from the flow rate meter 32. The processor 66 may compute the corrected analyte concentration based on empirical models to estimate the effect of fouling, convection, and osmosis on analyte recover, considering the tracer concentration and flow rate data. The paper "Utilizing transmembrane convection to enhance solute sampling and delivery by microdialysis: Theory and in vitro validation," by Peter M. Bungay et al., Journal of Membrane Science 348 (2010), pp. 131-149, which is incorporated herein by reference in its entirety, models the transmembrane convention at the microdialysis probe membrane 24.

In various embodiments, the control circuit 38 may be connected to (either via a wired or wireless connection) the supply pump 12. The control circuit 38 may receive flow rate data from the supply pump and/or output commands to the supply pump 12 to vary the flow rate from the supply pump 12. Based on the input flow rate from the supply pump 12, and based on the initial tracer concentration of the perfusate, the control circuit can determine the difference between the input (perfusate) tracer concentration and output (dialysate) tracer concentration. If the input tracer concentration (from the supply pump 12 before the probe 16) approaches the output tracer concentration (after the probe 16), fouling is obstructing the pores of the membrane 24 of the probe 16.

In one embodiment, sensitive detection of partial membrane fouling is achieved by changing inlet flow rate and measuring tracer concentration. Membrane fouling will affect analyte recovery directly or indirectly by changing convection and osmosis effects. For example, as membrane fouling occurs, convective effects are diminished due to the reduction in pore sizes. These indirect effects will occur before the fouling begins to decrease analyte recovery by decreasing effective membrane permeability. Currently there is no method to detect partial membrane fouling. In microdialysis, however, analyte recovery and tracer loss are both dependent on flow rate. One can take advantage of this dependency to measure small amounts of membrane fouling. Slow buffer flow rates allow more time for equilibration and thus increase analyte recovery and tracer loss from the perfusate. However, increasingly faster buffer flow rates lessen equilibration time and hence decrease exchange across the membrane. By making multiple dynamic measurements (i.e., at increasing flow rates), a series of analyte recovery and tracer loss curves can be generated automatically by the control circuit 38 (e.g., by the processor 66 executing instructions stored in the memory 42). A downward shift in the curves will reveal limited analyte and tracer diffusion, indicating increased membrane fouling.

In one embodiment, osmosis and convection can be distinguished from each other by increasing the inlet flow rate in the perfusate tubing 14 and measuring the outlet flow rate of the dialysate in the dialysate tubing 18. By examining the relationship between flow rates before and after the microdialysis probe 16, net fluid shift into or out of the probe 16 can be determined. This net fluid shift (if any) can be determined by the control circuit 38 using the perfusate flow rate data from the supply pump 12 and the dialysate flow rate data from the flow rate meter 32. If there is no fluid shift at all, then the plot of the two flow rates will fall along the diagonal line that begins at the origin. All points above the line mean that there is net flow out of the probe 16. Conversely, points below the line mean that there is net flow into the probe 16. By using increasing flow rates to increase pressure inside the probe 16, pressure-driven leak from the probe 16 (convection) will increase. Therefore, as inlet flow rate increases, if the outlet flow rate increases by a factor greater than 1×, then convection dominates the system. Yet if the outlet flow rate increases by a factor smaller than 1×, then osmosis dominates the system.

In one embodiment, a multitude of different in-line sensors can be incorporated with the microdialysis system 10. Other potential in-line sensors include neurotransmitters, drug sensors, metabolite sensors, electrolyte sensors, organ injury marker sensors (e.g., troponin sensors for heart damage etc.), tumor marker sensors, such as protein, DNA or RNA fragment, cytokine, chemokine, and growth factor sensors (e.g., markers of inflammation and other processes).

According to various embodiments, the present invention is directed to a microdialysis system comprising: (i) a microdialysis probe comprising a semipermeable membrane, wherein the microdialysis probe is implantable into a surrounding environment; (ii) a supply pump for supplying a perfusate to the microdialysis probe via perfusate tubing, the perfusate comprising real-time detectable tracer molecules, whereby, when the perfusate is pumped through the microdialysis probe, a portion of the tracer molecules are exchanged across the semipermeable membrane of the microdialysis probe into the surrounding environment, and analyte molecules from the surrounding environment are exchanged across the semipermeable membrane of the microdialysis probe into the microdialysis probe, thereby producing a dialysate; (iii) dialysate tubing for carrying the dialysate from the microdialysis probe; (iv) means for generating real time tracer concentration data (e.g., a tracer concentration meter) for the tracer molecules in the dialysate in the dialysate tubing; and (v) a control circuit in communication with the means for generating real time tracer concentration data, wherein the control circuit is for determining a real-time tracer concentration for the dialysate in the dialysate tubing based on the real-time tracer concentration data.

In various implementations, the microdialysis system may further comprise means for generating real-time flow rate data (e.g., a flow rate meter) for the dialysate in the dialysate tubing, wherein the control circuit is in communication with the means for generating real-time flow rate data, and wherein the control circuit is for determining a real-time flow rate of the dialysate in the dialysate tubing based on the real-time flow rate data. The control circuit may control operations of the tracer concentration meter and the flow rate meter. The real-time detectable tracer molecules may comprise fluorescent tracer molecules.

The tracer concentration meter may comprise: (i) a light source for directing light energy at a first side of the dialysate tubing; and (ii) a photo-sensor, facing a second side of the dialysate tubing that is different from the first side of the dialysate tubing, and wherein the photo-sensor is for sensing light energy emitted by the fluorescent tracer molecules in the dialysate in response to being illuminated with the light energy from the light source. The photo-sensor may comprise a CMOS image sensor or a photodiode. The flow rate meter may comprise a second photo-sensor that is a known distance downstream the dialysate tubing from the light source, wherein the second photo-sensor is in communication with the control circuit. The control circuit may determine the real-time flow rate of the dialysate based a time period that it takes for a photobleached plug in the dialysate, created by the light energy from the light source, to reach the second photo-sensor.

The microdialysis system may further comprise an analyte concentration meter in communication with the control circuit, wherein: the analyte concentration meter is for measuring a concentration of the analyte in the dialysate tubing; and the control circuit is for calculating a corrected analyte concentration based on inputs from the analyte concentration meter, the flow rate meter, and the tracer concentration meter. In such an embodiment, the tracer molecules may comprise fluorescein molecules and the analyte molecules may comprise glucose molecules.

In various embodiments, the flow rate meter comprises: a heater; and a temperature sensor that is a known distance downstream the dialysate tubing from the heater, wherein the heater and the temperature sensor are in communication with the control circuit. In such an embodiment, the control circuit is for determining the real-time flow rate of the dialysate based a time period that it takes for a thermal plug in the dialysate, created by heat from the heater, to reach the temperature sensor.

The microdialysis system may further comprise an analyte concentration meter in communication with the control circuit, wherein the analyte concentration meter is for measuring a concentration of the analyte in the dialysate tubing. In addition, the control circuit may calculate a corrected analyte concentration based on inputs from the analyte concentration meter, the flow rate meter, and the tracer concentration meter. The analyte concentration meter may comprise a glucose meter, for example.

According to other embodiments, the present invention is directed to a microdialysis method comprising the steps of: (i) supplying a perfusate from a supply pump to a microdialysis probe via perfusate tubing, wherein the microdialysis probe comprises a semipermeable membrane, and wherein the microdialysis probe is implantable into a surrounding environment, and wherein the perfusate comprises real-time detectable tracer molecules, whereby, when the perfusate is pumped through the microdialysis probe, a portion of the tracer molecules are exchanged across the semipermeable membrane of the microdialysis probe into the surrounding environment, and analyte molecules from the surrounding environment are exchanged across the semipermeable membrane of the microdialysis probe into the microdialysis probe, thereby producing a dialysate; (ii) carrying the dialysate from the microdialysis probe in dialysate tubing; (iii) generating real time tracer concentration data for the tracer molecules in the dialysate in the dialysate tubing; and (iv) determining a real-time tracer concentration for the dialysate in the dialysate tubing based on the real-time tracer concentration data.

In various implementations, the microdialysis method further comprises: generating real-time flow rate data for the dialysate in the dialysate tubing; and determining a real-time flow rate of the dialysate in the dialysate tubing based on the real-time flow rate data. Generating the real-time tracer concentration data may comprise the steps of: directing light energy from a light source at a first side of the dialysate tubing; and sensing by a photo-sensor light energy emitted by the fluorescent tracer molecules in the dialysate in response to being illuminated with the light energy from the light source, wherein the photo-sensor faces a second side of the dialysate tubing that is different from the first side of the dialysate tubing. Determining the real-time flow rate may comprise determining a time period that it takes for a plug in the dialysate to travel a known distance in the dialysate tubing. The plug may comprise a photobleached plug or a thermal plug, for example.

The microdialysis method may further comprise measuring a concentration of the analyte in the dialysate tubing with an analyte concentration meter. In addition, the microdialysis method may further comprise calculating a corrected analyte concentration based on the concentration of the analyte from the analyte concentration meter, the flow rate data, and the tracer concentration data.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A microdialysis system comprising:
   a microdialysis probe comprising a semipermeable membrane, wherein the microdialysis probe is implantable into a surrounding environment;
   a supply pump for supplying a perfusate to the microdialysis probe via perfusate tubing, the perfusate comprising real-time detectable tracer molecules, whereby, when the perfusate is pumped through the microdialysis probe, a portion of the tracer molecules are exchanged across the semipermeable membrane of the microdialysis probe into the surrounding environment, and analyte molecules from the surrounding environment are exchanged across the semipermeable membrane of the microdialysis probe into the microdialysis probe, thereby producing a dialysate;
   dialysate tubing for carrying the dialysate from the microdialysis probe such that the dialysate flows through the dialysate tubing;
   means for generating real-time tracer concentration data for the tracer molecules in the dialysate as the dialysate is flowing through the dialysate tubing;
   means for generating real-time flow rate data for the dialysate as the dialysate is flowing through the dialysate tubing, wherein the dialysate flows through the means for generating real-time tracer concentration data and the means for generating real-time flow rate data sequentially; and
   a control circuit in communication with the means for generating real-time tracer concentration data and the means for generating real-time flow rate data, wherein the control circuit is for determining a real-time tracer concentration for the dialysate in the dialysate tubing based on the real-time tracer concentration data and for determining a real-time flow rate of the dialysate in the dialysate tubing based on the real-time flow rate data.

2. The microdialysis system of claim 1, wherein the means for generating real-time tracer concentration data for the tracer molecules in the dialysate comprises a tracer concentration meter.

3. The microdialysis system of claim 2, wherein the means for generating real-time flow rate data comprises a flow rate meter.

4. The microdialysis system of claim 3, wherein the control circuit is for controlling operations of the tracer concentration meter and the flow rate meter.

5. The microdialysis system of claim 3, wherein the real-time detectable tracer molecules comprise fluorescent tracer molecules.

6. The microdialysis system of claim 5, wherein the tracer concentration meter comprises a fluorometer.

7. The microdialysis system of claim 5, wherein the tracer concentration meter comprises:
   a first light source for directing light energy at a first side of the dialysate tubing; and
   a first photo-sensor, facing a second side of the dialysate tubing that is different from the first side of the dialysate tubing, and wherein the first photo-sensor is for sensing light energy emitted by the fluorescent tracer molecules in the dialysate in response to being illuminated with the light energy from the first light source.

8. The microdialysis system of claim 7, wherein the first photo-sensor comprises a CMOS image sensor, and wherein the control circuit is in communication with the CMOS image sensor.

9. The microdialysis system of claim 7, wherein the first photo-sensor comprises a photodiode, and wherein the control circuit is in communication with the photodiode.

10. The microdialysis system of claim 7, wherein the flow rate meter comprises:
    a second light source, separate from the first light source of the tracer concentration meter; and
    a second photo-sensor that is a known distance downstream the dialysate tubing from the second light source, wherein the second photo-sensor is in communication with the control circuit.

11. The microdialysis system of claim 10, wherein the control circuit is for determining the real-time flow rate of the dialysate based a time period that it takes for a photobleached plug in the dialysate, created by the light energy from the second light source, to reach the second photo-sensor.

12. The microdialysis system of claim 11, wherein the first photo-sensor is the second photo-sensor.

13. The microdialysis system of claim 11, further comprising an analyte concentration meter in communication with the control circuit, wherein:
    the analyte concentration meter is for measuring a concentration of the analyte in the dialysate tubing; and
    the control circuit is for calculating a corrected analyte concentration based on inputs from the analyte concentration meter, the flow rate meter, and the tracer concentration meter.

14. The microdialysis system of claim 13, wherein the tracer molecules comprise fluorescein molecules and the analyte molecules comprises glucose molecules.

15. The microdialysis system of claim 7, wherein the flow rate meter comprises:
    a heater; and
    a temperature sensor that is a known distance downstream the dialysate tubing from the heater, wherein the heater and the temperature sensor are in communication with the control circuit.

16. The microdialysis system of claim 15, wherein the control circuit is for determining the real-time flow rate of the dialysate based a time period that it takes for a thermal plug in the dialysate, created by heat from the heater, to reach the temperature sensor.

17. The microdialysis system of claim 3, further comprising an analyte concentration meter in communication with the control circuit, wherein the analyte concentration meter is for measuring a concentration of the analyte in the dialysate tubing.

18. The microdialysis system of claim 17, wherein the control circuit is for calculating a corrected analyte concentration based on inputs from the analyte concentration meter, the flow rate meter, and the tracer concentration meter.

19. The microdialysis system of claim 18, wherein the tracer molecules comprise fluorescein molecules and the analyte molecules comprises glucose molecules.

20. The microdialysis system of claim 19, wherein the analyte concentration meter comprises a glucose meter.

21. The microdialysis system of claim 17, wherein the control circuit is in communication with the supply pump.

22. The microdialysis system of claim 2, wherein the control circuit comprises a RF transceiver circuit for transmitting data wirelessly to a remote device.

23. The microdialysis system of claim 1, wherein:
the real-time detectable tracer molecules comprise radioactive tracer molecules; and
the means for generating real time tracer concentration data comprises a radiation detector.

24. The microdialysis system of claim 1, wherein:
the real-time detectable tracer molecules comprise electrolyte molecules; and
the means for generating real time tracer concentration data comprises an electrical conductivity meter.

25. The microdialysis system of claim 1, wherein the dialysate flows through the means for generating real-time flow rate data before flowing through the means for generating real-time tracer concentration data.

26. A microdialysis method comprising:
supplying a perfusate from a supply pump to a microdialysis probe via perfusate tubing, wherein the microdialysis probe comprises a semipermeable membrane, and wherein the microdialysis probe is implantable into a surrounding environment, and wherein the perfusate comprises real-time detectable tracer molecules, whereby, when the perfusate is pumped through the microdialysis probe, a portion of the tracer molecules are exchanged across the semipermeable membrane of the microdialysis probe into the surrounding environment, and analyte molecules from the surrounding environment are exchanged across the semipermeable membrane of the microdialysis probe into the microdialysis probe, thereby producing a dialysate;
carrying the dialysate from the microdialysis probe in dialysate tubing such that the dialysate flows through the dialysate tubing;
generating real-time tracer concentration data for the tracer molecules in the dialysate as the dialysate flows through the dialysate tubing;
determining a real-time tracer concentration for the dialysate in the dialysate tubing based on the real-time tracer concentration data;
generating real-time flow rate data for the dialysate in the dialysate tubing as the dialysate flows through the dialysate tubing; and
determining a real-time flow rate of the dialysate in the dialysate tubing based on the real-time flow rate data.

27. The microdialysis method of claim 26, wherein the real-time detectable tracer molecules comprise fluorescent tracer molecules.

28. The microdialysis method of claim 27, wherein generating the real-time tracer concentration data comprises:
directing light energy from a light source at a first side of the dialysate tubing; and
sensing by a photo-sensor light energy emitted by the fluorescent tracer molecules in the dialysate in response to being illuminated with the light energy from the light source, wherein the photo-sensor faces a second side of the dialysate tubing that is different from the first side of the dialysate tubing.

29. The microdialysis method of claim 28, wherein the photo-sensor comprises a CMOS image sensor.

30. The microdialysis method of claim 28, wherein determining the real-time flow rate comprises determining a time period that it takes for a plug in the dialysate to travel a known distance in the dialysate tubing.

31. The microdialysis method of claim 30, wherein the plug comprises a photobleached plug.

32. The microdialysis method of claim 30, wherein the plug comprises a thermal plug.

33. The microdialysis method of claim 26, further comprising measuring a concentration of the analyte in the dialysate tubing with an analyte concentration meter.

34. The microdialysis method of claim 33, further comprising calculating a corrected analyte concentration based on the concentration of the analyte from the analyte concentration meter, the flow rate data, and the tracer concentration data.

35. The microdialysis method of claim 34, wherein the tracer molecules comprise fluorescein molecules and the analyte molecules comprises glucose molecules.

36. The microdialysis method of claim 35, wherein the analyte concentration meter comprises a glucose meter.

37. The microdialysis method of claim 33, further comprising varying a flow rate from the supply pump.

38. The microdialysis method of claim 26, wherein the control circuit comprises a RF transceiver circuit for transmitting data wirelessly to a remote device.

39. The microdialysis method of claim 26, wherein the real-time detectable tracer molecules comprise radioactive tracer molecules.

40. The microdialysis method of claim 26, wherein the real-time detectable tracer molecules comprise electrolyte molecules.

* * * * *